(12) United States Patent  
Suzuki (10) Patent No.: US 7,052,485 B2  
(45) Date of Patent: May 30, 2006

(54) BRIEF-TYPE DIAPER (75) Inventor: Seiji Suzuki, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 10/993,128

(22) Filed: Nov. 22, 2004

(65) Prior Publication Data  
US 2005/0124956 A1 Jun. 9, 2005

Related U.S. Application Data (63) Continuation of application No. PCT/JP2003/06293, filed on May 20, 2003.

(30) Foreign Application Priority Data  
May 22, 2002 (JP) ............................. 2002-147756

(51) Int. Cl.  
A61F 13/15 (2006.01)

(52) U.S. Cl. ..................................... 604/396

(58) Field of Classification Search ................ 604/396, 604/385.01  
See application file for complete search history.

(56) References Cited

U.S. PATENT DOCUMENTS 4,735,624 A * 4/1988 Mazars ...................... 604/378  
4,935,021 A * 6/1990 Huffman et al. ....... 604/385.26  
5,576,091 A * 11/1996 Zajaczkowski et al. ..... 428/192  
5,864,890 A * 2/1999 Niedermeyer .................. 2/403

FOREIGN PATENT DOCUMENTS

| EP | 1108371 A1 * | 6/2001 |
|---|---|---|
| EP | 1199060 A1 * | 4/2002 |
| JP | 06-296638 | 10/1994 |
| JP | 2572744 | 1/1997 |
| JP | 09-056747 | 3/1997 |
| JP | 2002-119534 | 4/2002 |
| JP | 2002-242001 | 8/2002 |
| JP | 2002-242001 A | 8/2002 |

* cited by examiner

Primary Examiner—Tatyana Zalukaeva  
Assistant Examiner—Ginger Chapman  
(74) Attorney, Agent, or Firm—Lowe Hauptman & Berner, LLP (57) ABSTRACT A brief-type diaper has pre-girth parts (4, 4') located vertically, and a pre-crotch part (5) located between the pre-girth parts and provided with substantially V-shaped recesses (6) in the front and rear body sides, respectively. An absorber is disposed in a brief-type diaper precursor (1) where pre-leg openings (7) are made. The precursor (1) is folded vertically along the center line X—X so that the pre-girth parts (4,4') and the pre-crotch part (5) are overlapped. Subsequently, the side fringe parts (4a, 5a) are bonded to form a waist opening thus obtaining a panty type diaper in which joints (11, 11) are formed in the front and rear bodies and no joint exist in the left and right bodies of the girth area.

20 Claims, 7 Drawing Sheets

BRIEF-TYPE DIAPER

CROSS-REFERENCE TO RELATED APPLICATIONS

This application is a Continuation of International Application No. PCT/JP2003/06293 filed May 20, 2003, which application published in Japanese on Nov. 27, 2003 as WO 2003/096950 A1 under PCT Article 21 (2). The International Application PCT/JP2003/06293 is based upon and claims the benefit of priority from Japanese Patent application No. 2002-147756 filed on May 22, 2002, the entire contents of which is incorporated herein by reference.

FIELD OF THE INVENTION

The invention relates to a brief-type diaper, and more particularly, to a diaper which is molded into the form of a brief by folding an absorbent for absorbing body fluids in a multilayer at the center of a pre-form blank for a brief-type diaper and by cementing together side edge portion of the pre-form blank for a brief-type diaper.

RELATED ART

Figure 13:
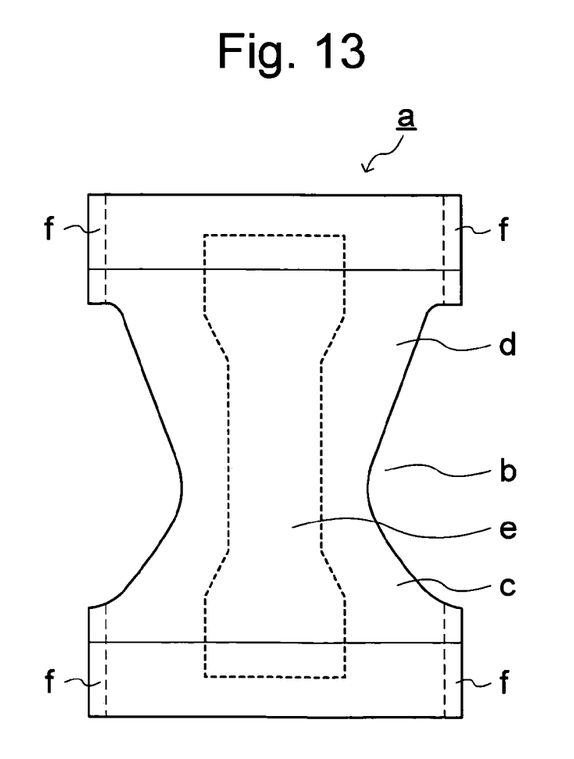
FIG. 13 is a developed plan view of conventional brief-type diaper

A diaper, such as that shown in, e.g., FIG. 13 (JP06-296638A), is available as a diaper of this type. The drawing shows a sheet into which the diaper is developed. A bow-shaped notch "b" is formed at either side edge of a sheet "a." An absorbent "e" is provided so as to spread across a front abdominal region "c" and a rear abdominal region "d." The sheet "a" is vertically folded in two, and side edge portions "f" are cemented together, thereby forming a waist opening and leg openings.

In the case of this diaper, both side edge portion "f" of the respective front and rear abdominal regions "c" and "d" are cemented together, and hence cemented lines possessing rigidity are present so as to stretch from the waist opening to the leg openings. For this reason, a wearer has an unusual feeling around his/her legs.

When the wearer wears the diaper, the diaper is often pulled up by pinching the right-side and left-side portions located in the vicinity of the waist opening. At that time, there arises the problem of a cemented section f having rigidity hindering the wearer from pinching the waist opening, thereby posing difficulty in pulling the diaper upward. Further, since the entire diaper is formed flat, a space for receiving and holding excretions is not formed. Hence, when attempting to get out of his/her diaper, the wearer experiences the inconvenience of the excretions adhering to the wearer's body.

In order to avoid the inconvenience, there has been proposed a technique as described in Japanese Patent No. 2572744. According to the technique, an opening is formed in a front sheet within a center crotch area of a diaper. Elastic members are provided on both adjacent sides of the opening in a longitudinal direction (front and rear direction) of the diaper, thereby imparting tension to the front side sheet. When the diaper is in use, the front side sheet located within the crotch area is separated from a rear sheet and an absorbent, thereby gathering excretions within the crotch area.

However, when body pressure is exerted on the diaper while the wearer wears the diaper, a pocket structure—in which the front sheet is separated from the rear sheet and the absorbent—is collapsed. Hence, a surface area to be used for absorbing body fluids such as urine is reduced, and the diaper becomes vulnerable to leakage. Moreover, since the diaper has the opening, a problem of an increase in manufacturing costs also arises.

SUMMARY OF THE INVENTION

The invention has been conceived in view of the foregoing drawbacks and provides a brief-type diaper which eliminates occurrence of the unusual feeling, which would otherwise arise around the legs, which is superior in ease of wearing, as well as receive and hold the excretion with created pocket while the diaper is formed.

In order to solve the problem, the present inventors have found that a brief-type diaper having no cemented sections on right and left abdominal regions in a girth section, while obtaining created pocket which can receive and hold the excretion, is obtained by folding a pre-form blank for the diaper along the axis of symmetry and cementing side edge portion of the pre-form blank, wherein the pre-form blank has an outer sheet constituting an exterior, an inner sheet which comes into contact with a wearer, an absorbent for absorbing body fluids, an elastic member for causing portions of the outer and inner sheets to contract and extend, and a pair of leg openings through which the wearer's legs penetrate. On the basis of this finding, the present invention have come to complete the present invention.

Equivalently, the brief-type diaper of the invention is provided on the basis of the idea that a pair of leg openings are formed in advance in a pre-form blank for a brief-type diaper and the side edge portion are cemented together by folding the pre-form blank along an intermediate position between the pair of leg openings.

More specifically, the invention provides the following features:

(1) A brief-type diaper having an outer sheet constituting an exterior, an inner sheet which comes into contact with a wearer, an absorbent for absorbing body fluids, an elastic member for causing portions of the outer and inner sheets to contract and extend, and a pair of leg openings through which the wear's legs penetrate, wherein the absorbent is arranged such that a portion of the absorbent is located between the pair of leg openings; and a cemented section is provided in a front abdominal region of the brief-type diaper so as to extend from the waist opening to a position between the pair of leg openings, and another cemented section is provided in a rear abdominal region of the brief-type diaper so as to extend from the waist opening to the position between the pair of leg openings.

According to the invention (1), the cemented sections are provided so as to extend from the waist opening to the crotch section by avoiding leg openings and across the front and rear abdominal regions. No cemented sections are provided on right and left abdominal regions of the girth section (more specifically, the both side area of girth section) so as to extend from the waist opening to the crotch section. Therefore, when a wearer wears the diaper, he/she can readily pull up the diaper while pinching the lateral portion of the waist opening with the fingers. Thus, the diaper becomes easier to wear. Further, the wearer does not have any unusual feeling around his/her legs upon wearing them.

In the invention, the term "front abdominal region" means a surface of a brief-type diaper facing an abdominal area when the diaper is viewed from above. The term "rear abdominal region" means a rear surface of the diaper opposite the front abdominal region. Also the term "right and left abdominal regions" means a surface of brief-type diaper facing right and left of body side when the diaper is viewed from above.

(2) The brief-type diaper according to (1), wherein the cemented sections are continuous fibers which extend across substantial center sections of the front and rear abdominal regions in a direction in which the brief-type diaper is to be worn.

According to the invention (2), the cemented sections are continuous fibers which extend across substantial center sections of the front and rear abdominal regions in a direction in which the brief-type diaper is to be worn.

Therefore, the cemented sections exist across the center sections of the front and rear abdominal regions so as to extend from the waist opening to the crotch section. Further, no cemented sections are provided on both lateral sides of the girth section, and hence the wearer does not have any unusual feeling around his/her legs while wearing the diaper. No cemented sections exist on right and left abdominal regions of the girth section (more specifically, the both side portion of girth section) so as to extend from the waist opening to the leg openings. Hence, when wearing the diaper, the wearer can readily pull up the diaper while pinching on the lateral portion at the waist opening with the fingers. Thus, the diaper becomes easy to wear. The term "fiber" describes that fiber characteristics with thin elongated string-like or thin band-like condition, which the thickness and width are not particularly limited. Also the term "direction in which the brief-type diaper is to be worn" describes the vertical direction upon wearing the brief-type diaper.

(3) A pre-form blank for a brief-type diaper which is a substantially-rectangular single cloth and in which a substantial center of a side of a part of the pre-form blank to act as the front abdominal region assumes the shape of a substantially-V-shaped indentation, and a substantial center of a side of the other part of the pre-form blank to act as the rearward abdominal region also assumes the shape of a substantially-V-shaped indentation; the pre-form blank having a pre-girth section to act as a girth section, pre-leg opening sections to act as leg opening sections, and a pre-crotch section to act as a crotch section; further comprising the pre-girth section being present in the form of an upper rectangular portion and a lower rectangular portion, wherein an elastic member is provided in the pre-girth section in a stretched manner, and the pre-leg openings being present in the form of holes and at positions which are symmetrical about the axis of symmetry of the pre-form blank for a brief-type diaper; and the pre-crotch section being located at an intermediate position in the pre-girth section and having substantially-V-shaped indentations along both sides of the parts of the pre-form blank to act as the front and rear abdominal regions.

The pre-form blank for a brief-type diaper according to (3) is a substantially-rectangular single cloth, wherein a substantial center of a side (a left or right side of the pre-form blank for a brief-type diaper) of a part of the pre-form blank to act as the front abdominal region assumes the shape of a substantially-V-shaped indentation, and a substantial center of a side of the other part of the pre-form blank to act as the rearward abdominal region also assumes the shape of a substantially-V-shaped indentation. The pre-form blank for a brief type diaper has a pre-girth section to act as a girth section, pre-leg opening sections to act as leg opening sections, and a pre-crotch section to act as a crotch section. Further, the pre-girth section is present in the form of an upper substantially-rectangular portion and a lower substantially-rectangular portion, wherein an elastic member is provided in the pre-girth section in a stretched manner. The pre-leg openings are present in the form of a pair holes and at positions which are symmetrical about the axis of symmetry of the pre-form blank for a brief-type diaper. The pre-crotch section is located at an intermediate position in the pre-girth section and has substantially-V-shaped indentations along both sides of the parts of the pre-form blank to act as the front and rear abdominal regions.

The absorbent is provided on the pre-form blank fro a brief-type diaper and at the intermediate position between the pre-leg openings such that the longitudinal direction of the absorbent coincides with the direction of axis of symmetry of the pre-form blank for a brief-type diaper. The pre-form blank for a brief-type diaper is folded vertically along the axis of symmetry of the pre-form blank, thereby cementing together the side edge portion of the pre-girth section in the front abdominal region and the side of the pre-girth section in the rear abdominal region and cementing together the side edge of the pre-crotch section in the rear abdominal region and the side of the pre-crotch section in the rear abdominal region. As a result, the waist opening is formed, thereby forming a brief-type diaper having the leg openings. The pre-form blank is folded vertically along the intermediate position between the pair of pre-leg sections (more specifically, the axis of symmetry of the pre-form blank for a brief-type diaper). Hence, the side edge portions of the pre-girth and pre-crotch sections in the front abdominal region and the side edge portions of the same in the rear abdominal region are cemented together. Consequently, cemented sections are formed in the front and rear abdominal regions of the brief-type diaper.

In the invention, the term "pre-form blank for a brief-type diaper" means a member to be used for forming a brief-type diaper; a single cloth when it is developed by separating cemented sections of the diaper. The term "pre-girth section" means a section which is to act as a girth section when the pre-form blank for a brief-type diaper is formed into a diaper. The term "pre-leg opening" means a section which is to act as a leg opening when the pre-form blank for a brief-type diaper is formed into a diaper. The term "pre-crotch section" means a section which is to act as a crotch section when the pre-form blank for a brief-type diaper is formed into a diaper. The vertical direction signifies the Y direction, provided that the axis of symmetry of the pre-form blank for a brief-type diaper is taken as the X direction and a direction orthogonal to the X direction is taken as a Y direction. Further, the horizontal direction signifies the X direction, provided that the axis of symmetry of the pre-form blank for a brief-type diaper is taken as the X direction and a direction orthogonal to the X direction is taken as the Y direction. Moreover, the holes of the pre-leg openings mean holes which constitute leg openings when the pre-form blank for a brief-type diaper is formed into a brief-type diaper. The geometry of the pre-leg opening includes a mere cut (slit) as well as a circular shape of an opening.

(4) A pre-form blank for a brief-type diaper which is a substantially-oval single cloth wherein a substantial center of each respective side to act as the front and rear abdominal region assumes the shape of a substantially-V-shaped indentation, the pre-form blank having a pre-girth section to act as a girth section, pre-leg opening sections to act as leg opening sections, and a pre-crotch section to act as a crotch section, further comprising the pre-girth section being present in the form of an upper substantially-semicircular portion and a lower substantially-semicircular portion, wherein an elastic member is provided in the pre-girth section in a stretched manner and the pre-leg openings being present in the form of holes and at positions which are symmetrical about the axis of symmetry of the pre-form blank for a brief-type diaper; and the pre-crotch section being located at an intermediate position in the pre-girth section and having substantially-V-shaped indentations along both sides of the parts of the pre-form blank to act as the front and rear abdominal regions.

Pre-form blank for a brief-type diaper according to the invention (4) is a substantially-oval single cloth, wherein a substantial center of each side of the pre-form blank to act as the front abdominal region assumes the shape of a substantially-V-shaped indentation, and a substantial center of a side of the other part of the pre-form blank to act as the rearward abdominal region also assumes the shape of a substantially-V-shaped indentation. The pre-form blank has a pre-girth section to act as a girth section, pre-leg opening sections to act as leg opening sections, and a pre-crotch section to act as a crotch section. Further, the pre-girth section is present in the form of an arc portion of a substantially-semicircular upper portion and an arc portion of a substantially-semicircular lower portion, wherein an elastic member is provided in the pre-girth section in a stretched manner. The pre-leg openings are present in the form of holes and at positions which are symmetrical about the axis of symmetry of the pre-form blank for brief-type diaper. The pre-crotch section is located at an intermediate position in the pre-girth section and has substantially-V-shaped indentations along both sides of the pre-form blank to act as the front and rear abdominal regions.

Therefore, the absorbent is provided on the pre-form blank for brief-type diaper and at the intermediate position between the pre-leg openings such that the longitudinal direction of the absorbent coincides with the direction of axis of symmetry of the pre-form blank for a brief-type diaper. The pre-form blank for a brief-type diaper is folded vertically along the axis of symmetry of the pre-form blank, thereby cementing together the side edge portion of the pre-crotch section. Thus, the waist opening is formed, thereby forming a brief-type diaper having the leg openings. Here, the pre-form blank is folded vertically along the intermediate position between the pair of pre-leg sections (more specifically, the axis of symmetry of the pre-form blank for a brief-type diaper). Hence, the side edges of the pre-girth and pre-crotch sections in the front abdominal region and the side edges of the same in the rear abdominal region are cemented together. Consequently, cemented sections are formed in the front and rear abdominal regions of the brief-type diaper.

(5) The brief-type diaper according to (1) or (2), wherein the brief-type diaper is formed from the single outer sheet constituting the pre-girth section and the pre-crotch section, the elastic member provided on an upper surface of the outer sheet in an extended state, the inner sheet which is attached integrally to the outer sheet and the elastic member and is substantially identical in size and shape with the outer sheet, and the absorbent provided in a substantial center of an upper surface of the inner sheet; and wherein both side edges of the pre-girth section and/or both side edges of the pre-crotch section are fixedly cemented together, to thereby constitute a waist opening.

The brief-type diaper of the invention (5) is formed from the single outer sheet constituting the pre-girth section and the pre-crotch section; the elastic member provided on an upper surface of the outer sheet in an extended state; the inner sheet which is attached integrally to the outer sheet and the elastic member and is substantially identical in size and shape with the outer sheet; and the absorbent provided in a substantial center of an upper surface of the inner sheet. Both side edge portions of the pre-girth section and/or both side edge portions of the pre-crotch section are fixedly cemented together, to thereby constitute a waist opening.

The pre-form blank is folded vertically along the intermediate position between the pair of pre-leg sections (more specifically, the axis of symmetry of the pre-form blank for a brief-type diaper). Hence, both side edge portions of the pre-girth and/or pre-crotch sections (side edge portions located in the front and rear abdominal regions) are cemented together. Consequently, the resultantly-cemented sections are formed in the front and rear abdominal regions of the brief-type diaper.

Here the term "upper surface" of the inner and outer sheet means to describe the wearer's lateral body side of the outer and inner sheet.

(6) The brief-type diaper according to (1) or (2), wherein the brief-type diaper is formed from the single outer sheet constituting the pre-girth section and the pre-crotch section, the elastic member provided on an upper surface of the outer sheet in an extended state, the absorbent provided in a substantial center of an upper surface of the inner sheet, and the inner sheet which is substantially identical in size and shape with the outer sheet, which has an opening section in a substantial center thereof, and which is attached integrally to the outer sheet and the elastic member such that the opening section covers an outer brim of the absorbent; and wherein both side edge portions of the pre-girth section and/or both side edge portions of the pre-crotch section are fixedly cemented together, to thereby constitute a waist opening.

The brief-type diaper of the invention (6) is formed from the single outer sheet constituting the pre-girth section and the pre-crotch section; the elastic member provided on an upper surface of the outer sheet in an extended state, and the absorbent provided in a substantial center of an upper surface of the inner sheet; and the inner sheet which is substantially identical in size and shape with the outer sheet, which has an opening section in a substantial center thereof, and which is attached integrally to the outer sheet and the elastic member such that the opening section covers an outer brim of the absorbent. Both side edge portions of the pre-girth section and/or both side edge portions of the pre-crotch section of pre-form blank for brief-type diaper are fixedly cemented together, to thereby constitute a waist opening.

The pre-form blank is folded vertically along the intermediate position between the pair of pre-leg sections (more specifically, the axis of symmetry of the pre-form blank for brief-type diaper). Hence, both side edges of the pre-girth and/or pre-crotch sections (more specifically, the side edges located in the front and rear abdominal regions) are cemented together. Consequently, the resultantly-cemented sections are formed in the front and rear abdominal regions of the brief-type diaper.

(7) The brief-type diaper according to (1) or (2), wherein both longitudinal ends of the absorbent are split into two in a widthwise direction; a non-split section of the absorbent is located in a center of the crotch section; and the split sections of the absorbent are arranged in a center of the front abdominal region and that of the rear abdominal region so as to straddle the cemented sections.

According to the brief-type diaper of the invention (7), both longitudinal ends of the absorbent are split in two in a widthwise direction, and the non-split section of the absorbent is located in a center of the crotch section. Further, the split sections of the absorbent are arranged in a center of the front abdominal region and that of the rear abdominal region so as to straddle the cemented sections.

Therefore, the cemented sections are provided in the center sections of the front and rear abdominal regions of brief-type diaper. The split sections of the absorbent are arranged so as to straddle the cemented sections. Therefore, when a brief-type diaper is formed from the pre-form blank, the absorbent is pulled by cementing action, whereby bulging sections are formed from the absorbent in the crotch section of the front abdominal region and in that of the rear abdominal region. Excretions, such as fecal matter, are stored and held by the bulging section located in the rearward abdominal region of the diaper so as not to come into contact with the body of the wearer. Further, a penis is accommodated within the bulging section of the front abdominal region of the diaper.

(8) The brief-type diaper according to (7), wherein a leakage prevention wall is provided along longitudinal side edges of the absorbent over the entire length thereof.

According to the invention (8), a leakage prevention wall is provided along longitudinal side edges of the absorbent, wherein the absorbent is comprised of pre-form blank for a brief-type diaper, over the entire length thereof. Thus, when the pre-form blank for a brief-type diaper is formed into a brief-type diaper, the leakage prevention wall is formed around the absorbent provided in the diaper so as to extend from the longitudinal center of the absorbent over the entire length thereof. As a result, seepage excretions such as urine, which would otherwise arise from edges of the leg openings, can be prevented further.

(9) The pre-form blank for brief-type diaper according to (3), wherein the elastic member is provided along an edge of the pre-girth section in an extended manner.

According to the invention (9), pre-form blank for brief-type diaper, formed from the elastic member provided along the edge of the pre-girth section in a stretched manner. Therefore, when the pre-form blank is folded and the side edges of the blank are cemented together, to thereby form a waist opening, the elastic member contracts, thereby rendering the girth section elastic. Therefore, the diaper conforms to the skin of the wearer when the diaper is worn. The elastic members are preferably made such that the degree of elongation and stress change from the waist region to the girth region. As a result, the degree of fastening changes from the waist region to the girth region, thereby causing the diaper to conform much better to the figure of the wearer's body.

In the invention, the term "waist region" means a part of the diaper which conforms to a position on the body above the hip bone. Further, the term "girth section" means a part of the diaper which conforms to the area of the body ranging from the hip bone to the crotch.

(10) The brief-type diaper for brief-type diaper according to (4), wherein the elastic member is provided along a substantially-semicircular outer brim of the pre-girth section in a stretched manner.

According to the invention (10), the elastic member of pre-form blank for brief-type diaper is provided along the outer periphery of the pre-girth section in a stretched manner. Therefore, when the pre-form blank is folded and the side edge portions of the pre-crotch section are cemented together, to thereby form a brief-type diaper, the elastic member contracts, thereby rendering the girth section elastic. Therefore, the diaper conforms to the skin of the wearer when the diaper is worn. The elastic members are preferably made such that the degree of elongation and stress change from the waist region to the girth region. As a result, the degree of fastening changes from the waist region to the girth region, thereby causing the diaper to conform much better to the figure of the wearer's body.

DESCRIPTION OF THE PREFERRED EMBODIMENT

Embodiments of the invention will be described in detail hereinbelow by reference to the drawings.

[First Embodiment]

Figure 1:
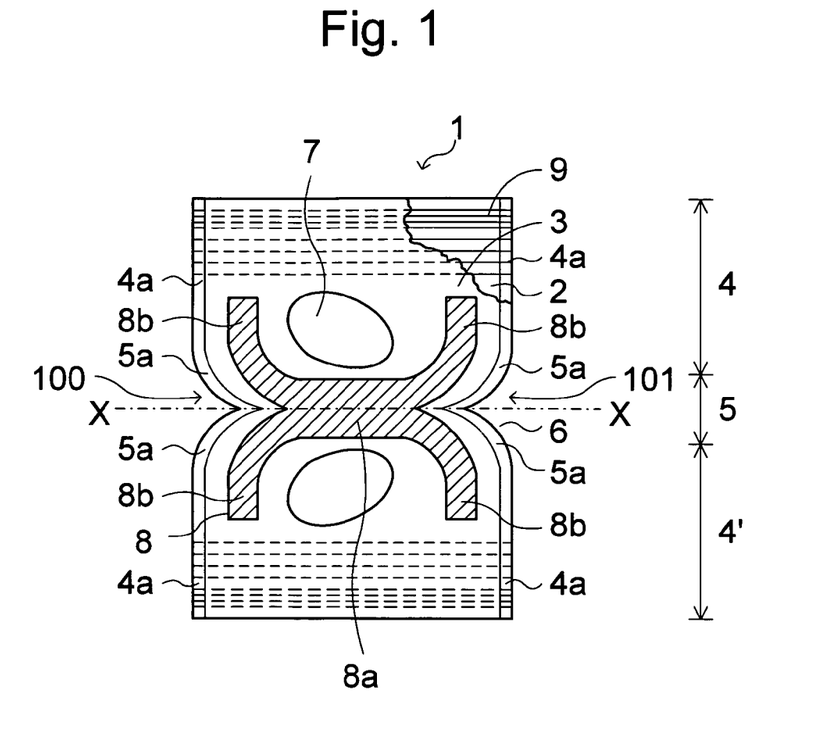
FIG. 1 is a partially fragmentary developed plan view showing a developed state of a brief-type diaper according to a first embodiment of the invention.
Figure 2:
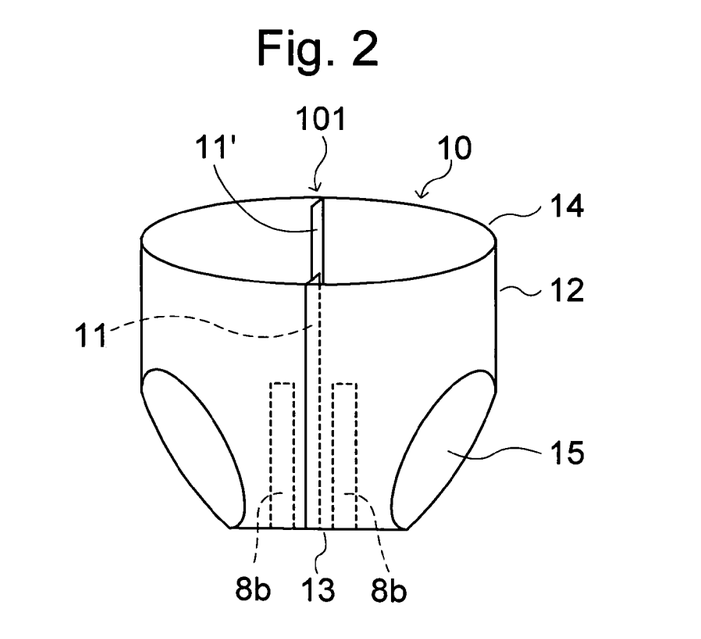
FIG. 2 is a schematic perspective view of the brief-type diaper of the first embodiment when viewed from the front.
Figure 3:
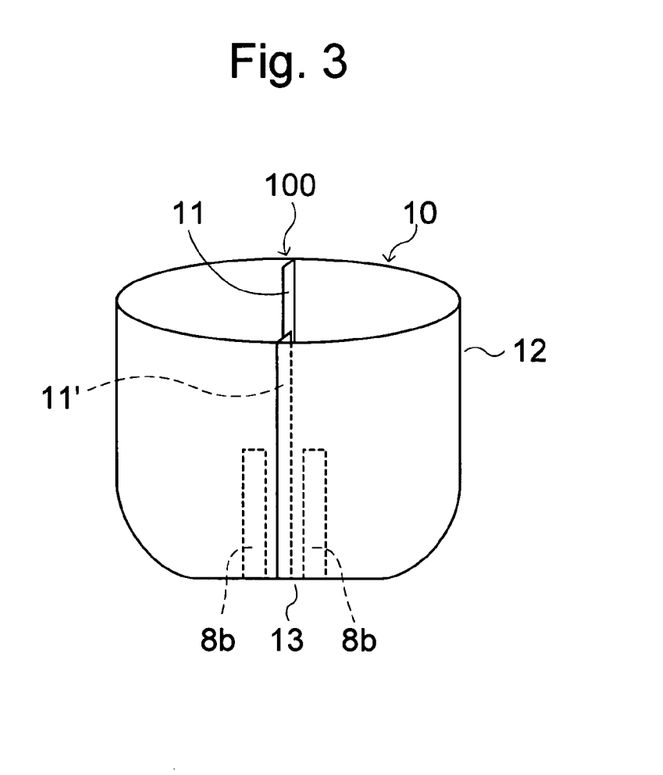
FIG. 3 is a schematic perspective view of the brief-type diaper of the first embodiment when viewed from the rear.
Figure 4:
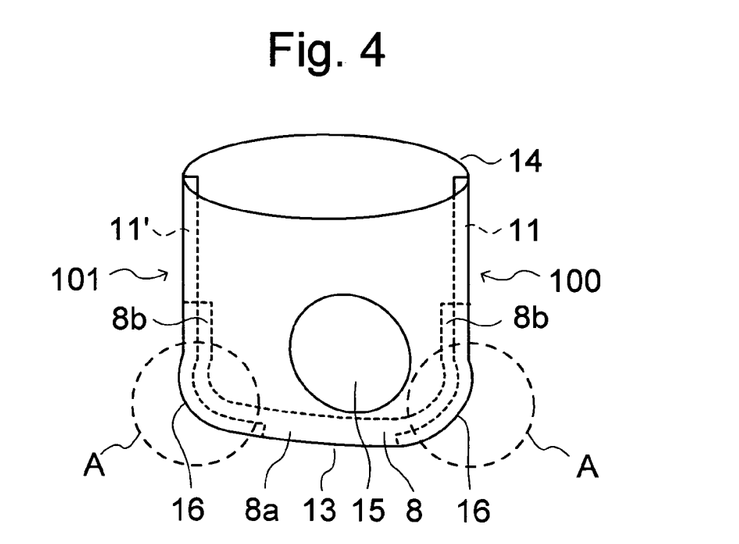
FIG. 4 is a schematic perspective view of the brief-type diaper of the first embodiment when viewed from the side.
Figure 5:
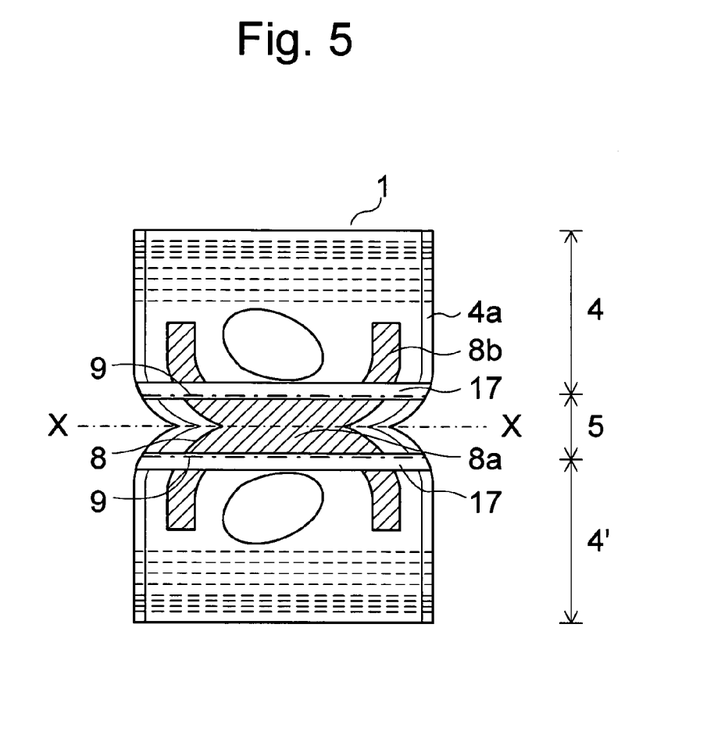
FIG. 5 is a descriptive view showing a case where a leakage prevention wall is provided on the brief-type diaper of the first embodiment shown in FIG. 1.
Figure 6:
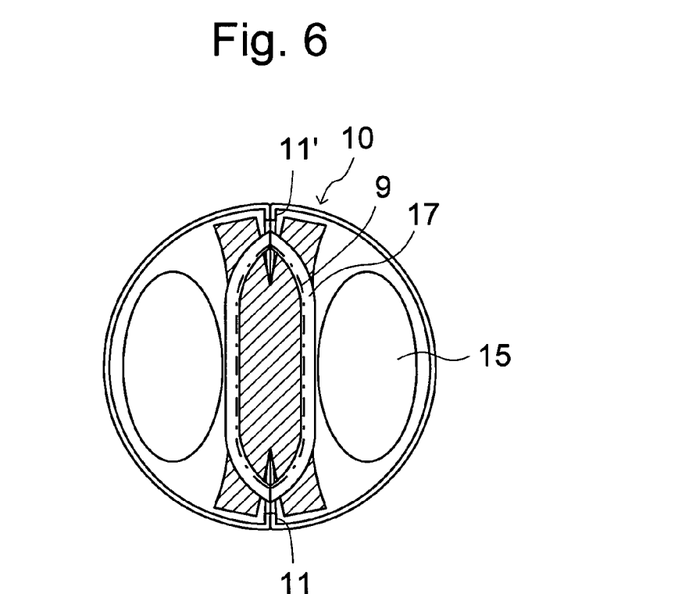
FIG. 6 is a plan view of a brief-type diaper obtained as a result of the brief-type diaper shown in FIG. 5 having been formed.
Figure 7:
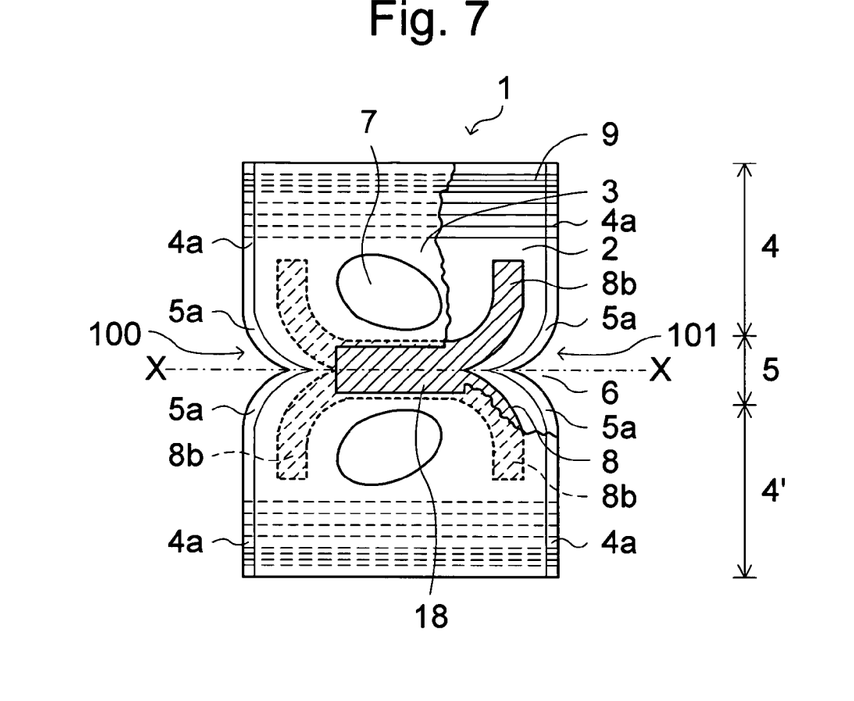
FIG. 7 is a partially fragmentary developed plan view showing a modification of the first embodiment according to the invention.

FIG. 1 is a partially fragmentary developed plan view showing a developed state of a brief-type diaper according to a first embodiment of the invention; FIG. 2 is a schematic perspective view of the brief-type diaper according to the invention of the first embodiment when viewed from the front; FIG. 3 is a schematic perspective view of the brief-type diaper according to the invention of the first embodiment when viewed from the rear; FIG. 4 is a according to the invention schematic perspective view of the brief-type diaper of the first embodiment when viewed from the side; FIG. 5 is a descriptive view showing a case where a leakage prevention wall is provided on the brief-type diaper of the first embodiment shown in FIG. 1; FIG. 6 is a plan view of a brief-type diaper obtained as a result of the diaper shown in FIG. 5 having been formed; FIG. 7 is a partially fragmented developed plan view showing a modification of the first embodiment according to the invention;

With in reference to numeral 1 of FIG. 1, designates a pre-form blank for a brief-type diaper, formed from an outer sheet 2 constituting an exterior, and an inner sheet 3 to be brought into contact with a wearer's skin wherein the outer sheet 2 and the inner sheet 3 assume a substantially-rectangular shape. The pre-form blank for a brief-type diaper comprises substantially-rectangular pre-girth sections 4, 4' located at upper and lower portions of the pre-form blank for brief-type diaper 1; and a swath pre-crotch section 5 which is located between the pre-girth sections 4, 4' and has substantially-V-shaped indentations 6, one being located along side edges of the part of the pre-form blank for a brief-type diaper which is to constitute a front abdominal region and the other being located along side edges of the part of the pre-form blank which is to constitute a rear abdominal region 100, 101. A pair of pre-leg openings 7 are formed in the form of substantially-oval holes at respective positions on the pre-girth sections 4, 4', the positions being symmetrical with respect to an axis of symmetry X—X of the pre-form blank 1 for a brief-type diaper. The geometry of the pre-leg opening 7 is not limited to a substantially-oval shape but may be a circular or semi-circular shape, or a simple cut line (slit).

Reference numeral 8 designates an absorbent, and the absorbent 8 comprises a liquid-impervious back sheet, a liquid-pervious top sheet, and an absorbent core interposed between the sheets. Each longitudinal end of the absorbent core is split in two in a transverse direction of the absorbent core. A non-split section 8a of the absorbent 8 is provided at the center of the pre-crotch section 5 such that a longitudinal direction of the absorbent 8 is oriented horizontally. Split sections 8b are provided along respective side edge portions 5a, of the substantially-V-shaped indentations 6 formed at the respective ends of the pre-crotch section 5.

Inner sheet 3 is bonded integrally to the upper surface of the outer sheet 2 (Hereinafter, upper surface is referred to as body side surface of the wearer), and the absorbent 8 is laminated onto the upper surface of the inner sheet 3. Alternatively, a waterproof back sheet, which will be described later and constitutes the absorbent 8, may be interposed between the outer sheet 2 and the inner sheet 3. Thus, even when excretions, such as body fluids, have erroneously leaked out, the back sheet will prevent seepage the excretions to the outer sheet 2. Elastic members 9 are horizontally provided on the upper surface of the sheet 2 along the upper end of the pre-girth section 4 and the other lower end of the pre-girth section 4' in a stretched manner. When the pre-form blank has been formed into a brief-type diaper, the elastic members 9 undergo extension and shrinkage, thereby rendering a girth portion of the diaper resilient. The elastic members 9 to be provided at the pre-girth sections 4, 4' are preferably made such that the degree of elongation and stress change from the waist region to the girth region. As a result, the degree of fastening changes from the waist region to the girth region, thereby causing the diaper to conform much better to the figure of the wearer's body. In other words, allowing appropriate fit just enough from brief-type diaper to be fall off and be able to fit at the ease around the waist. The way to change the fitness around the waist and girth region may also be achieved by selecting the number of elastic members, intervals at which the elastic members are to be stretched, the thickness of the elastic members, and materials of the elastic members, as required, rather than changing the degree of its elongation. In addition, settings on degree of elongation and stress of elastic member 9 can be same.

In the specification, the horizontal direction signifies an X direction, provided that the axis of symmetry of the pre-form blank for a brief-type diaper 1 is taken as the X direction and a direction orthogonal to the X direction is taken as a Y direction. Further, the vertical direction signifies the Y direction, provided that the axis of symmetry of the pre-form blank 1 is taken as the X direction and a direction orthogonal to the X direction is taken as a Y direction. The term "waist region" is the area of the diaper fits above the hipbone. The term "girth region" is the area of the diaper fits between hipbone and crotch area of the body upon wearing them.

When a brief-type diaper 10 shown in FIG. 2 formed from the pre-form blank 1, the non-split section 8a of the absorbent 8 comes to the center of the pre-crotch section 5 on the upper surface of the inner sheet 3 of the pre-form blank 1. The split sections 8b are provided along respective side edges 5a, of the substantially-V-shaped indentations 6 formed at the respective ends of the pre-crotch section 5 and are bonded to the inner sheet 3. The pre-crotch section 5 is folded vertically along the axis of symmetry X—X. The pre-girth sections 4, 4' are superimposed one on the other and side edge portions 4a of the superimposed pre-girth sections 4, 4' are cemented together, and the side edge portions 5a of the superimposed pre-crotch section 5 are cemented together, thereby forming a waist opening 14. A cementing method to be employed in this embodiment includes thermal fusing, ultrasonic fusing, and bonding involving use of an adhesive such as a hot melt adhesive.

FIGS. 2 and 3 show the thus-formed brief-type diaper. Cemented sections 11, 11' are formed in the brief-type diaper 10 so as to extend straight from the waist opening 14 to a crotch section 13 in the longitudinal direction along the center section of the front abdominal region and that of the rear abdominal region 100, 101.

As detail shown in FIG. 4, the cemented sections 11, 11' extend from the waist opening 14 to portions of the crotch section 13 within the front and rear abdominal regions 100, 101. The absorbent 8 is provided so as to extend across the front and rear abdominal regions 100, 101 via the crotch section 13. As shown in FIGS. 2 through 4, the non-split section 8a of the absorbent 8 is placed in the center area of the crotch section 13. Further, the split sections 8b of the absorbent 8 are placed such that one split section 8b extends from the girth section 12 in the front abdominal region 100 to the crotch section 13 so as to straddle the cemented section 11, 11' and such that the other split section 8b extends from the girth section 12 in the rear abdominal region 101 to the crotch section 13 so as to straddle the cemented section 11, 11'. Thus, the absorbent 8 is split, and the crotch section 13 is formed in a curved shape. Hence, the outer sheet 2 and the inner sheet 3 are pushed by the absorbent 8 in the crotch section 13 between the front and rear abdominal regions 100, 101 (within the areas encircled by dotted lines in FIG. 4), thereby forming bulging sections 16, 16.

In the brief-type diaper 10, the rigid cemented sections 11, 11' extend straight in the longitudinal direction along the center sections of the front and rear abdominal regions 100, 101 so as to avoid the leg openings 15. Hence, the wearer does not have any unusual feeling around the legs.

Further, the cemented section 11 is located at the center of the front abdominal region 100, and the cemented section 11' is located at the center of the rear abdominal region 101. Thus, the cemented sections 11, 11' are spaced apart from lateral portions of the pre-form blank 1 in the girth section 12 when viewed from the front and back. Therefore, when the wearer wears the diaper, the cemented sections 11, 11' do not hinder the wearer from pulling up the diaper 10. At that time, the cemented sections 11, 11' do not catch any part of the wearer's body.

Further, the bulging sections 16, 16 arise in the crotch section 13 of the front and rear abdominal regions 100, 101, whereby spaces are defined between the absorbent 8 and the wearer's skin. Since the wearer's penis or excretions such as fecal matter are housed in the spaces, the degree to which the excretions adhere to the wearer's skin can be diminished. Further, the absorbent 8 of the crotch section 13 assumes a flat surface which is likely to absorb body fluids such as urine.

Alternatively, a leakage prevention wall 17 may be provided beforehand on either longitudinal side of the absorbent 8 in the longitudinal direction thereof. As shown in FIG. 5, if the leakage prevention wall 17 is provided along both side edges of the absorbent 8, the leakage prevention wall 17 will be provided along a boundary between the absorbent 8, pre-girth sections 4, 4' of the pre-from blank for a diaper 1 and the pre-crotch section 5. When the pre-form blank for a brief-type diaper 1 is formed into the brief-type diaper 10, the extremities of the leakage prevention walls 17 are closed at the cemented sections 11, 11'. When viewed from above, the leakage prevention wall 17 assumes a substantially-oval shape such as that shown in FIG. 6. The leakage prevention wall 17 is made of hydrophobic nonwoven fabric cloth. The elastic member 9 is provided along a free longitudinal side of the leakage prevention wall 17 in an elongated state. When the pre-form blank 1 is formed into the diaper-type brief 10, elastic member 9 will contract to raise the leakage prevention wall 17. Provision of the leakage prevention wall 17 yields the effect of the ability to prevent leakage of body fluids such as urine from the absorbent 8.

The outer sheet 2 and the inner sheet 3, which are members for constituting these brief-type diapers 10, are preferably made of gas-permeable nonwoven fabric cloth, more preferably of hydrophobic nonwoven fabric cloth. For example, the nonwoven fabric cloth includes spun bond nonwoven fabric cloth made of polypropylene or the like; through-air nonwoven fabric cloth made of fibers, such as polyethylene fibers, polypropylene fibers, polyethylene terephthalate fibers, or the like; and spun lace nonwoven fabric cloth. In addition, there may also be employed a complex sheet formed from nonwoven fabric cloth which includes elastomer or copolymer and possesses flexibility and an extensible characteristic—and a flexible film. Moreover, a liquid-impervious plastic film, for example, liquid impervious back sheet comprising absorbent 8 may be sandwiched between the outer sheet 2 and the inner sheet 3.

Absorbent 8 is formed from a rectangular or guitar-shaped absorbent core which is sandwiched between the liquid-impervious back sheet and the liquid-pervious top sheet such that each longitudinal end of the core is split from a longitudinal center in a transverse direction of the core. The liquid-impervious back sheet is nonwoven fabric cloth which has been subjected to water repellent finishing, a moisture-permeable plastic film having minute pores, or a layered product consisting from the fabric cloth and the plastic film. Nonwoven fabric cloth is usually used for the liquid-pervious top sheet. The absorbent core is preferably a core made by combined use of defibrated pulp and water-absorptive polymer. In addition, a core—which is formed from a mixture of cellulose fibers, thermoplastic resin, high-molecular water-absorptive polymer, heat-fusible fibers, and the like and which has been subjected to heat treatment—s also preferable. In the case of an absorbent into which several layers are stacked, a polymer may be located in an upper layer, an intermediate layer, or a lower layer. Alternatively, the polymer may be uniformly mixed with pulp. The water-absorptive polymer preferably has the capability of absorbing liquid which is 20 times or more the weight of the polymer and the property of gelation. Preferable water-absorptive polymer includes starch-acrylic acid (acrylate) graft copolymer, saponificated starch-acrylonitrile copolymer, crosslinked sodium carboxymethyl cellulose, and acrylic acid (acrylate) polymer.

The elastic members 9 are not limited to any particular material but are formed from any material, so long as the material possesses elasticity; for example, rubber yarn made of natural/synthetic rubber or polyurethane, a ribbon-shaped elastic body, heat-shrinkable material, and water-absorptive shrinkable fibers.

FIG. 7 shows a modification of the first embodiment. As shown in FIG. 7, the pre-form blank for a brief-type diaper 1 assumes a substantially-rectangular shape, formed from substantially-rectangular pre-girth sections 4, 4', the pre-girth section 4 being located at an upper position on the pre-form blank and the pre-girth section 4' being located at a lower position on the pre-form blank; the outer sheet 2 which is located at an intermediate position between the pre-girth sections 4, 4' and has the substantially-swath pre-crotch section 5 having at both ends thereof the substantially-V-shaped indentations 6, each indentation being provided along side edges of front and rear abdominal region 100, 101 sides of the pre-form blank; and the inner sheet 3 which is substantially identical in size and shape with the outer sheet 2 and has an opening section 18 which is formed in the center of the outer sheet (center of the pre-crotch section 5) and substantially identical in size with or slightly smaller than the absorbent 8. The pre-form blank may assume a structure in which the inner sheet 3 is integrally provided on the upper surface of the outer sheet 2. The elastic member 9 is provided horizontally in an extended state on the upper surface of the outer sheet 2 along the upper edge of the pre-girth section 4 and along the other lower edge of the pre-girth section 4'. The elastic members 9 to be provided at the pre-girth sections 4, 4' are preferably made such that the degree of elongation and stress change from the waist region to the girth region. As a result, the degree of fastening changes from the waist region to the girth region, thereby causing the diaper to conform much better to the figure of the wearer's body. Moreover, pair of pre-leg openings 7 is formed in the form of a substantially-oval hole at respective positions on the pre-girth sections 4, 4', the positions being symmetrical with respect to an axis of symmetry X—X of the pre-form blank 1. The geometry of the pre-leg opening 7 is not limited to a substantially-oval shape but may be a circular or semi-circular shape or a simple cut line (slit).

When a brief-type diaper is formed from the pre-form blank 1, the non-split section 8a of the absorbent 8 coincides with the opening section 18 of the inner sheet 3 at the center of the pre-crotch section 5 and between the outer sheet 2 and the inner sheet 3 of the pre-form blank 1. The split sections 8b are provided along the side edge portions 5a of the substantially-V-shaped indentations 6 formed at the respective ends of the pre-crotch section 5 and are bonded to the outer sheet 2 and the inner sheet 3. The pre-crotch section 5 is folded vertically along the axis of symmetry X—X. The pre-girth sections 4, 4' are superimposed one on the other. The side edge portions 4a of the superimposed pre-girth sections 4, 4' are cemented together, and the side edges 5a of the superimposed pre-crotch section 5 are cemented together, thereby forming the waist opening 14. A cementing method to be employed in this case includes thermal fusing, ultrasonic fusing, and bonding involving use of an adhesive such as a hot melt adhesive.

In this way, as in the case of the first embodiment, the cemented sections 11, 11' are formed in the thus-formed brief-type diaper of the modification, not illustrated, so as to extend straight from the waist opening 14 to a crotch section 13 in the longitudinal direction along the center section of the front abdominal region and that of the rear abdominal region 100, 101 (See FIG. 2 through 4).

The cemented sections 11, 11', as in the case of the first embodiment, extend from the waist opening 14 to portions of the crotch section 13 within the front and rear abdominal regions 100, 101. The absorbent 8 is provided so as to extend across the front and rear abdominal regions 100, 101 via the crotch section 13. The non-split section 8a of the absorbent 8 is placed in the center area of the crotch section 13. Further, the split sections 8b of the absorbent 8 are placed such that one split section 8b extends from the girth section 12 in the front abdominal region 100 to the crotch section 13 so as to straddle the cemented section 11 and such that the other split section 8b extends from the girth section 12 in the rear abdominal region to the crotch section 13 so as to straddle the cemented section 11'. Thus, the absorbent 8 is split, and the crotch section 13 is formed in a curved shape. Hence, the outer sheet 2 and the inner sheet 3 are pushed by the absorbent 8 in the crotch section 13 between the front and rear abdominal regions 100, 101, thereby forming the bulging sections 16, 16 (see FIG. 4).

In the brief-type diaper 10, the rigid cemented sections 11, 11' extend straight in the longitudinal direction along the center sections of the front and rear abdominal regions 100, 101 so as to avoid the leg openings 15. Hence, the wearer does not have any unusual feeling around the legs.

Further, the bulging sections 16 arise in the crotch section 5 of the front and rear abdominal regions 100, 101, whereby spaces are defined between the absorbent 8 and the wearer's skin. Since the wearer's penis or excretions such as fecal matter are housed in the spaces, the degree to which the excretions adhere to the wearer's skin can be diminished. Further, the absorbent 8 of the crotch section 13 assumes a flat surface which is likely to absorb body fluids such as urine.

Although not illustrated, even in the modification a leakage prevention wall 17 may be provided beforehand on either longitudinal side of the absorbent 8 in the longitudinal direction thereof, as in the case of the first embodiment. Provision of the leakage prevention wall 17 yields an effect of the ability to leak body fluids such as urine to the absorbent (see FIGS. 5 and 6).

[Second Embodiment]

Figure 8:
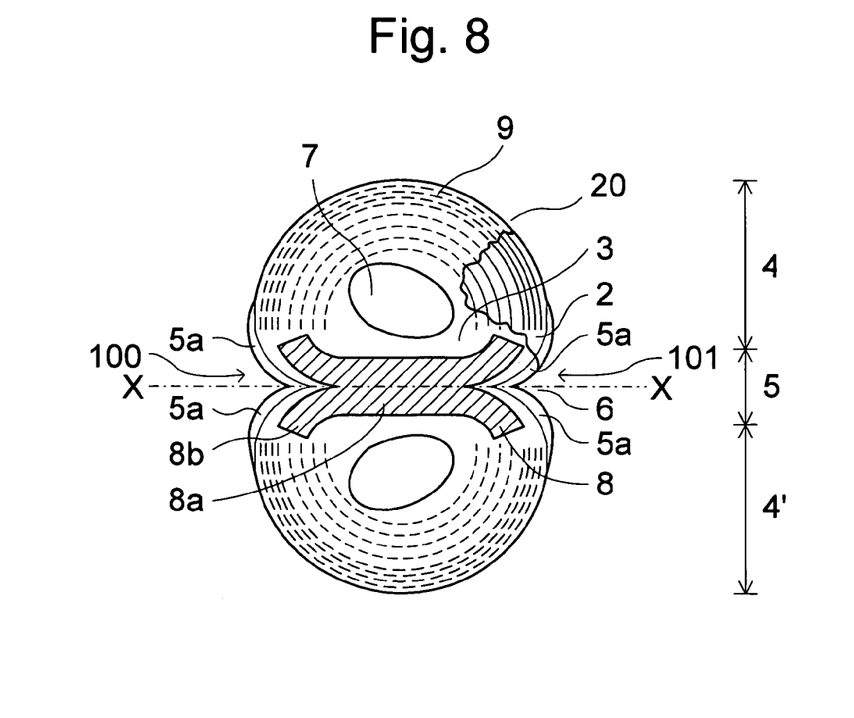
FIG. 8 is a partially fragmentary developed plan view showing the developed state of a brief-type diaper according to a second embodiment of the invention.
Figure 9A:
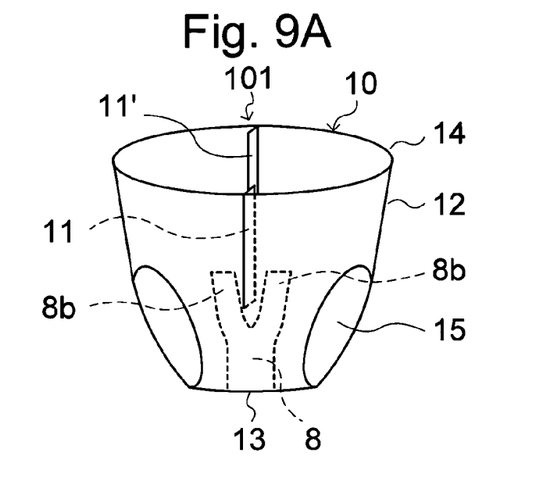
FIG. 9A is a schematic perspective view showing the second embodiment of the brief-type diaper when viewed from the front.
Figure 9B:
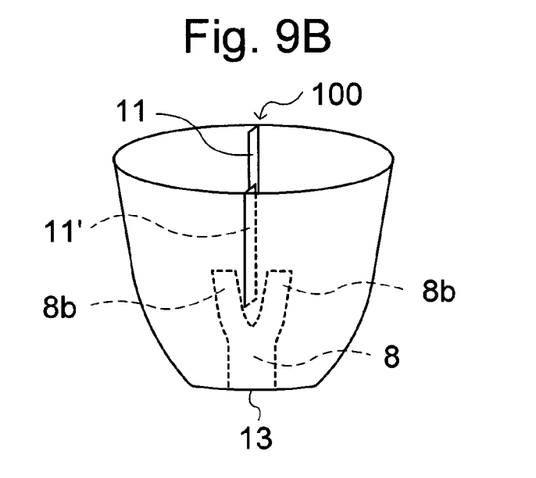
FIG. 9B is a schematic perspective view showing the second embodiment of the brief-type diaper when viewed from the rear.
Figure 9C:
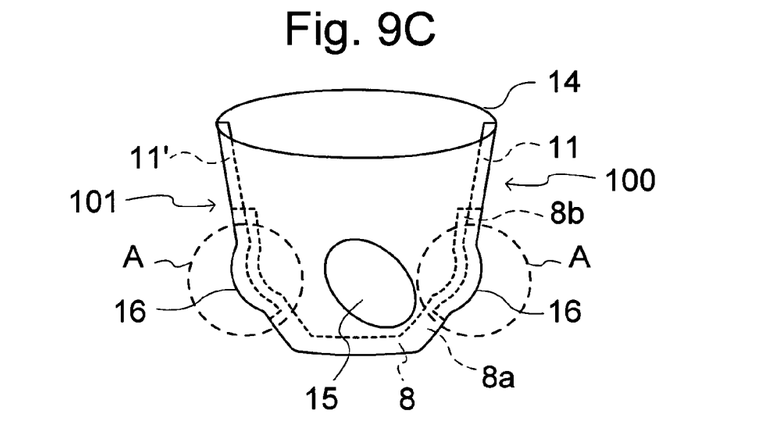
FIG. 9C is a schematic perspective view showing the second embodiment of the brief-type diaper when viewed from the side.
Figure 10:
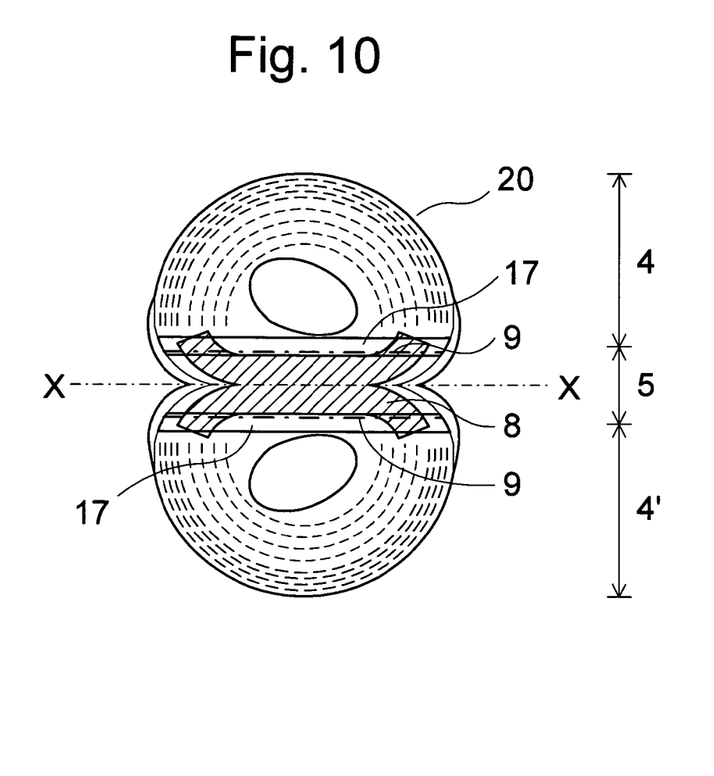
FIG. 10 is a descriptive view of the brief-type diaper of the second embodiment, showing a case where a leakage prevention wall is provided on the brief-type diaper.
Figure 11:
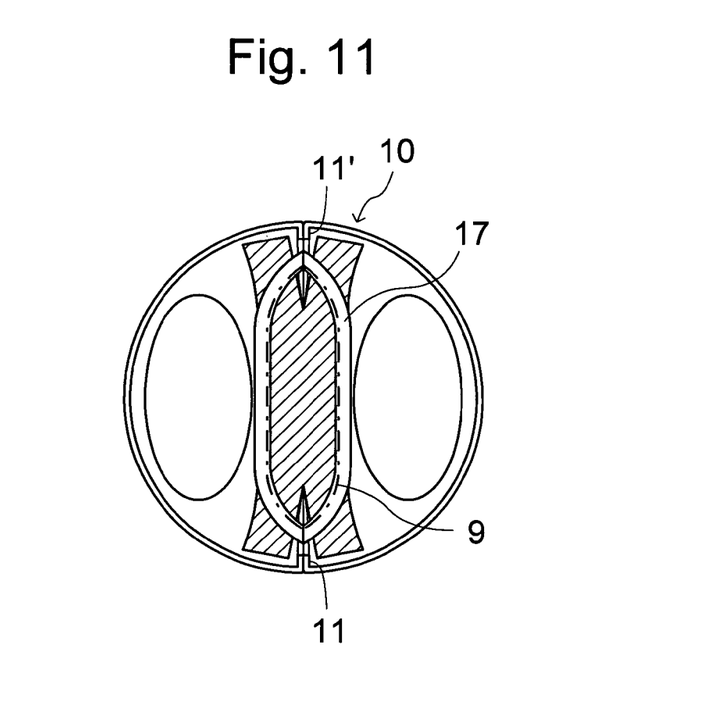
FIG. 11 is a plan view showing a brief-type diaper obtained as a result of the brief-type diaper shown in FIG. 10 being formed.
Figure 12:
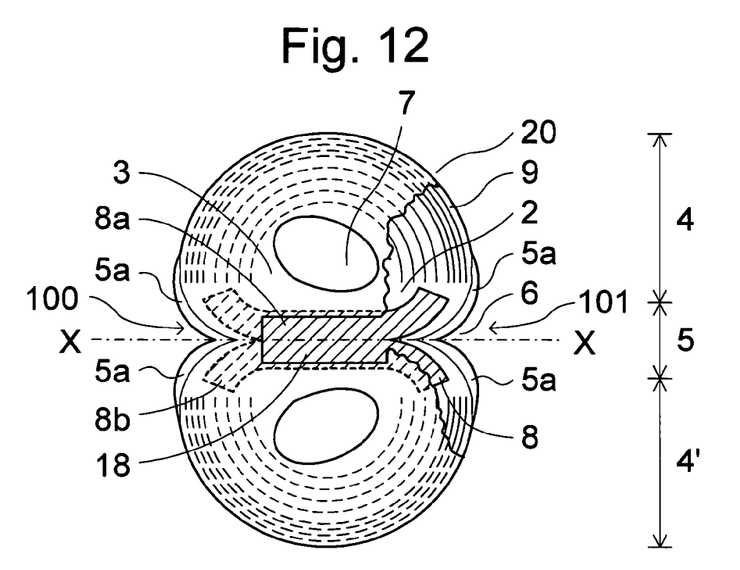
FIG. 12 is a partially fragmented developed plan view showing a modification of the second embodiment.

FIG. 8 provides a partially fragmented developed plan view of a brief-type diaper according to a second embodiment of the invention. FIG. 9A provides a schematic perspective view of the second embodiment viewed from front and FIG. 9B provides a schematic perspective view of the second embodiment viewed from rear side and FIG. 9C provides schematic perspective view of the second embodiment viewed from side. Also FIG. 10 is a descriptive view of the brief-type diaper of the second embodiment, showing a case where a leakage prevention wall is provided on the diaper, and FIG. 11 is a plan view showing a brief-type diaper obtained as a result of the brief-type diaper shown in FIG. 10 being formed, and FIG. 12 is a partially fragmented developed plan view showing a modification of the second embodiment. In the embodiment below, those constituent elements which are the same as those described in connection with the first embodiment are assigned the same reference numerals, and their explanations are omitted.

In FIG. 8, reference numeral 20 designates a pre-form blank for a brief-type diaper. The pre-form blank for a brief-type diaper 20 is constituted of the outer sheet 2 constituting an exterior, and the inner sheet 3 to be brought into contact with a wearer's skin. The outer sheet 2 and the inner sheet 3 assume a substantially-oval outer shape. The pre-form blank for a brief-type diaper 20 is a single cloth, wherein substantially-V-shaped indentations are formed at a substantial center of the pre-form blank existing between a part of the pre-form blank which is to act as the front abdominal region 100 and the other part of the pre-form blank which is to act as the rearward abdominal region 101. The pre-form blank for a brief-type diaper 20 comprises the substantially-semicircular pre-girth sections 4, 4' located at upper and lower portions of the pre-form blank for a brief-type diaper 20; and the substantially-swath pre-crotch section 5 which is located between the pre-girth sections 4, 4' and has substantially-V-shaped indentations 6, one being located along side edges of the part of the pre-form blank which is to constitute the front abdominal region 100 and the other being located along side edges of the part of the pre-form blank which is to constitute the rear abdominal region 101. A pair of pre-leg openings 7 are formed in the form of a substantially-oval hole at respective positions on the pre-girth sections 4, 4' so as to extend from the pre-crotch section 5 to the pre-girth sections 4, 4', the positions being symmetrical with respect to an axis of symmetry X—X of the pre-form blank for a brief-type diaper 20. The geometry of the pre-leg opening 7 is not limited to a substantially-oval shape but may be a circular or semi-circular shape or a simple cut line (slit).

The absorbent 8 comprises a liquid-impervious back sheet, a liquid-pervious top sheet, and an absorbent core interposed between the sheets. Each longitudinal end of the absorbent core 8 is split into two in a transverse direction of the absorbent core 8. The non-split section 8a of the absorbent 8 is provided at the center of the pre-crotch section 5 such that a longitudinal direction of the absorbent 8 is oriented horizontally. The split sections 8b are provided along the respective side edge portions 5a of the substantially-V-shaped indentations 6 formed at the respective ends of the pre-crotch section 5.

Inner sheet 3 is bonded integrally to the upper surface of the outer sheet 2, and the absorbent 8 is laminated onto the upper surface of the inner sheet 3. Alternatively, a waterproof back sheet, which constitutes the absorbent 8, may be interposed between the outer sheet 2 and the inner sheet 3. As a result, even when excretions, such as body fluids, have mistakenly leaked out, the back sheet will prevent seepage of the excretions to the outer sheet 2. The elastic members 9 are horizontally provided on the upper surface of the sheet 2 along the upper end of the pre-girth section 4 and the lower end of the pre-girth section 4' in a stretched manner. When the pre-form blank has been formed into a brief-type diaper, the elastic members 9 undergo extension and shrinkage, thereby rendering a girth portion of the diaper resilient. The elastic members 9 to be provided at the pre-girth sections 4, 4' are preferably made such that the degree of elongation and stress change from the waist region to the girth region. As a result, the degree of fastening changes from the waist region to the girth region, thereby causing the diaper to conform much better to the figure of the wearer's body.

When a brief-type diaper 10 is formed from the pre-form blank 20, the non-split section 8a of the absorbent 8 comes to the center of the pre-crotch section 5 on the upper surface of the inner sheet 3 of the pre-form blank for a brief-type diaper 20. The split sections 8b are provided along respective side edge portions 5a of the substantially-V-shaped indentations 6 formed at the respective ends of the pre-crotch section 5 and are bonded to the inner sheet 3. The pre-form blank 20 is folded vertically along the axis of symmetry X—X, thereby superimposing the pre-girth sections 4, 4' one on the other. The side edge portions 5a of the superimposed pre-crotch section 5 are cemented together, thereby forming the waist opening 14. A cementing method to be employed in this embodiment includes thermal fusing, ultrasonic fusing, and bonding involving use of an adhesive such as a hot melt adhesive.

FIGS. 9A to 9C show the thus-formed brief-type diaper 10. As shown in FIG. 9A to 9C, the brief-type diaper 10 has such a shape that the girth section 12 is slightly tapered toward the crotch section 13. The cemented sections 11, 11' are formed in the girth section 12 of the front and rear abdominal regions 100, 101, so as to extend straight from the waist opening 14 to the crotch section 13. The absorbent 8 is provided so as to extend across the front 100 and rear abdominal regions 101 via the crotch section 13. The split sections 8b of the absorbent 8 are placed such that one split section 8b extends from the girth section 12 in the front abdominal region to the crotch section 13 so as to straddle the cemented section 11 and such that the other split section 8b extends from the girth section 12 in the rear abdominal region to the crotch section 13 so as to straddle the cemented section 11'. Further, the non-split section 8a of the absorbent 8 is placed in the center area of the crotch section 13. Thus, the absorbent 8 is split, and the crotch section 13 is formed in a curved shape. As described in connection with the first embodiment, the outer sheet 2 and the inner sheet 3 are pushed by the absorbent 8 in the crotch section 13 (within the area encircled by a broken-line frame A in FIG. 9C) between the front 100 and rear abdominal regions 101, thereby forming the bulging sections 16, 16.

Alternatively, the leakage prevention wall 17 may be provided beforehand on either longitudinal side of the absorbent 8 in the longitudinal direction thereof. As shown in FIG. 10, if the leakage prevention wall 17 is provided along both side edges of the absorbent 8, the leakage prevention wall 17 will be provided along a boundary between the absorbent 8 and the pre-girth sections 4, 4' of the pre-from blank for a brief-type diaper 20. When the pre-form blank for a brief-type diaper 20 is formed into the brief-type diaper 10, the extremities of the leakage prevention walls 17 are closed at the cemented sections 11, 11'. When viewed from above, the leakage prevention wall 17 assumes a substantially-oval shape such as that shown in FIG. 11. The leakage prevention wall 17 is made of hydrophobic nonwoven fabric cloth. The elastic member 9 is provided along the free longitudinal side of the leakage prevention wall 17 in an elongated state. When the pre-form blank for a brief-type diaper 20 is formed into the diaper-type brief 10, the elastic member will contract and raise the leakage prevention wall 17. Provision of the leakage prevention wall 17 yields the effect of the ability to prevent leakage of body fluids such as urine from the absorbent 8.

Since the brief-type diaper 10 of the embodiment has the foregoing construction, the wearer does not feel any unusual feeling around his/her legs. Thus, the cemented sections 11, 11' are spaced apart from lateral portions of the waist opening 14. Therefore, when the wearer wears the brief-type diaper 10, he/she can readily pull up the diaper while pinching the lateral portion of the waist opening 14 with the fingers. Thus, the diaper becomes easier to wear. Further, the bulging sections 16 arise in the crotch section 13 of the cemented sections 11, 11', whereby spaces are defined between the absorbent 8 and the wearer's skin. Since excretions such as fecal matter are housed in the spaces, the degree to which the excretions adhere to the wearer's skin can be diminished.

FIG. 12 shows a modification of the second embodiment. The pre-form blank for a brief-type diaper 20 assumes a substantially-rectangular shape. The pre-form blank for a brief-type diaper is a single cloth, wherein substantially-V-shaped indentations 6 are formed at a substantial center of the pre-form blank for a brief-type diaper existing between a part of the pre-form blank for a brief-type diaper which is to act as the front abdominal region 100 and the other part of the pre-form blank which is to act as the rear abdominal region 101. The pre-form blank for a brief-type diaper 20 comprises the substantially-semicircular pre-girth sections 4, 4' located at upper and lower portions of the pre-form blank for a brief-type diaper 20; the outer sheet 2 formed from the substantially-swath pre-crotch section 5, the pre-crotch section being located between the pre-girth sections 4, 4' and having substantially-V-shaped indentations 6; that is, one being located along side edges of the part of the pre-form blank for the brief-type diaper which is to constitute the front abdominal region 100 and the other being located along side edges of the part of the pre-form blank for a brief-type diaper which is to constitute the rear abdominal region 101; and the inner sheet 3, in which the opening section 18 substantially identical in size with or slightly smaller than the absorbent 8 is formed in the center of the inner sheet 3 and in which the inner sheet 3 is placed integrally on the upper surface of the outer sheet 2. Further, the elastic members 9 are provided on the upper surface of the sheet 2 along the outer brim of the pre-girth section 4 and the outer brim of the pre-girth section 4' in a stretched manner. The elastic members 9 to be provided at the pre-girth sections 4, 4' are preferably made such that the degree of elongation and stress change from the waist region to the girth region. As a result, the degree of fastening changes from the waist region to the girth region, thereby causing the diaper to conform much better to the figure of the wearer's body. Moreover, the pre-leg openings 7 are formed in the form of a substantially-oval hole at respective positions on the pre-girth sections 4, 4', the positions being symmetrical with respect to an axis of symmetry X—X of the pre-form blank for a brief-type diaper 20. The geometry of the pre-leg opening 7 is not limited to a substantially-oval shape but may be a circular or semi-circular shape, or a simple cut line (slit).

When a brief-type diaper is formed from the pre-form blank for a brief-type diaper 20, the non-split section 8a of the absorbent 8 coincides with the opening section 18 of the inner sheet 3 at the center of the pre-crotch section 5 and between the outer sheet 2 and the inner sheet 3 of the pre-form blank for a brief-type diaper 20. The split sections 8b are provided along respective side edge portions 5a, 5a of the substantially-V-shaped indentations 6 formed at the respective ends of the pre-crotch section 5 and are bonded to the outer sheet 2 and the inner sheet 3. The pre-crotch section 5 is folded vertically along the axis of symmetry X—X. The pre-girth sections 4, 4' are superimposed one on the other and the side edges 5a of the superimposed pre-crotch section 5 are cemented together, thereby forming the waist opening 14. A cementing method to be employed in this case includes thermal fusing, ultrasonic fusing, and bonding involving use of an adhesive such as a hot melt adhesive.

In this way, as in the case of the second embodiment, the cemented sections 11, 11' are formed in the thus-formed brief-type diaper 10 of the modification so as to extend straight from the waist opening 14 to the crotch section 13 in the longitudinal direction along the center section of the front abdominal region 100 and that of the rear abdominal region 101 (see FIG. 9A through FIG. 9C).

As described in connection with the second embodiment, the thus-formed brief-type diaper 10 has such a shape that the girth section 12 is slightly tapered toward the crotch section 13. The cemented sections 11, 11' are formed in the girth section 12 of the front and rear abdominal regions 100, 101, so as to extend from the waist opening 14 to the crotch section 13. The absorbent 8 is provided so as to extend across the front and rear abdominal regions 100, 101, via the crotch section 13. The split sections 8b of the absorbent 8 are placed such that one split section 8b extends from the girth section 12 in the front abdominal region to the crotch section 13 so as to straddle the cemented section 11 and such that the other split section 8b extends from the girth section 12 in the rear abdominal region to the crotch section 13 so as to straddle the cemented section 11'. Further, the non-split section 8a of the absorbent 8 is placed in the center area of the crotch section 13. Thus, the absorbent 8 is split, and the crotch section 13 is formed in a curved shape. As described in connection with the second embodiment, the outer sheet 2 and the inner sheet 3 are pushed by the absorbent 8 in the crotch section 13 between the front and rear abdominal regions, thereby forming bulging sections (see FIG. 9C).

Although not illustrated, even in the modification the leakage prevention wall 17 may be provided beforehand on either longitudinal side of the absorbent 8 in the longitudinal direction thereof, as in the case of the second embodiment. Provision of the leakage prevention wall 17 yields an effect of the ability to leak body fluids such as urine to the absorbent 8 (see FIGS. 10 and 11).

Since the brief-type diaper 10 of the embodiment has the foregoing construction, the wearer does not feel any unusual feeling around his/her legs. Thus, the cemented sections 11, 11' do not exist between waist opening 14 and leg opening 15 at the right and left abdominal region of girth section 12 allowing the wearer to readily pull up the diaper 10 while pinching the lateral portion of the waist opening 14 with the fingers upon wearing the brief-type diaper 10. Thus, the diaper becomes easier to wear. Further, the bulging sections 16 arise in the crotch section 13 of the cemented sections, whereby spaces are defined between the absorbent 8 and the wearer's skin. Since excretions such as fecal matter are housed in the spaces, the degree to which the excretions adhere to the wearer's skin can be diminished.

As has been described, the brief-type diaper of the invention is constructed such that cemented sections are formed into continuous fibers which extend in the direction in which the brief-type diaper is to be worn, at the center section of the front and rearward abdominal regions of the diaper. The cemented sections are not formed on both sides of a girth. Namely, the cemented sections are not formed so as to extend from a waist opening to leg openings. Hence, the wearer does not have any unusual feeling around his/her legs. Since the cemented sections are not provided in a girth section of a left abdominal region and a girth section of a right abdominal region so as to extend from the waist opening to the leg openings, the wearer can readily pull up the diaper when wearing the diaper while pinching up the lateral portion of the waist opening with the fingers. Thus, the diaper becomes easy to wear.

The side edge portions of the pre-form blank for a brief-type diaper are cemented together at the center between the front and rearward abdominal sections. Each of split sections of an absorbent is split in two. Bulging sections are formed by the absorbent in these sections. Excretions, such as fecal matter, are stored and held by the bulging section located in the rearward abdominal region of the diaper so as not to come into contact with the body of the wearer. Further, a penis is accommodated in the bulging section of the front abdominal region of the diaper.

What is claimed is:

1. A brief-type diaper, comprising a single panel having an outer sheet defining an exterior of the diaper, an inner sheet adapted to come into contact with a wearer, an absorbent for absorbing body fluids, and a pair of leg openings;

wherein
   a portion of the absorbent is located between the leg openings;
   front edge sections of said panel are bonded together along a front bonding line and rear edge sections of said panel are bonded together along a rear bonding line to define a waist opening of said diaper;
   said front bonding line is provided in a front abdominal region of the diaper and extends from the waist opening to a first position between the leg openings;
   said rear bonding line is provided in a rear abdominal region of the diaper and extends from the waist opening to a second position between the leg openings; and
   said panel extends seamlessly from one of said leg openings to the other.

2. The diaper according to claim 1, wherein the bonding lines are continuous and extend substantially centrally of the front and rear abdominal regions in a direction in which the diaper is to be worn.

3. A diaper blank for forming a brief-type diaper, said blank being contoured by front, rear, upper, and lower edges and comprising an upper portion, a lower portion and an intermediate portion between said upper and lower portions;
   said front edge having a first, substantially-V-shaped indentation in a vicinity of a central line of said blank located in said intermediate portion, and said rear edge having a second, substantially-V-shaped indentation in the vicinity of said central line;
   elastic members being provided along said upper and lower edges which are adapted to define together a waist opening of said diaper;
   two leg holes located on opposite sides of said central line, each in one of said upper and lower portions; and
   said upper and lower portions being adapted to together define each of front and rear abdominal regions of the diaper, and said intermediate portion being adapted to define a crotch region of the diaper.

4. The blank according to claim 3, wherein said blank has a substantially-oval shape and said upper and lower portions are substantially-semicircular.

5. The diaper according to claim 1, wherein an elastic member is provided along a circumferential edge of the wais opening and sandwiched between the outer sheet and the inner sheet which is substantially identical in size and shape to the outer sheet.

6. The diaper according to claim 2, wherein an elastic member is provided along a circumferential edge of the wais opening and sandwiched between the outer sheet and the inner sheet which is substantially identical in size and shape to the outer sheet.

7. The diaper according to claim 1, wherein an elastic member is provided along a circumferential edge of the wais opening and sandwiched between the outer sheet and the inner sheet which is substantially identical in size and shape to the outer sheet, and which has an opening in a center thereof.

8. The diaper according to claim 2, wherein an elastic member is provided along a circumferential edge of the wais opening and sandwiched between the outer sheet and the inner sheet which is substantially identical in size and shape to the outer sheet, and which has an opening in a center thereof.

9. The diaper according to claim 2, wherein
both longitudinal ends of the absorbent are split into two in a widthwise direction;
a non-split section of the absorbent is located in a center of a crotch region of the diaper; and
the split sections of the absorbent are arranged in a center of the front abdominal region and that of the rear abdominal region so as to straddle the bonding lines.

10. The diaper according to claim 2, wherein
both longitudinal ends of the absorbent are split into two in a widthwise direction;
a non-split section of the absorbent is located in a center of a crotch region of the diaper; and
the split sections of the absorbent are arranged in a center of the front abdominal region and that of the rear abdominal region so as to straddle the bonding lines.

11. The diaper according to claim 9, futher comprising a leakage prevention wall provided along longitudinal side edges of the absorbent over the entire length thereof.

12. The brief-type diaper according to claim 10, futher comprising a leakage prevention wall provided along longitudinal side edges of the absorbent over the entire length thereof.

13. The blank according to claim 3, wherein the elastic members are provided along the upper and lower edges in a stretched state.

14. The blank according to claim 4, wherein the elastic members are provided along a substantially-semicircular outer brim of the upper and lower portions in a stretched state.

15. The blank according to claim 3, wherein said blank has a substantially rectangular shape and said upper and lower portions are substantially rectangular.

16. The blank according to claim 3, wherein each of said leg holes has a circumferential edge that extends seamlessly for full 360 degrees.

17. The blank according to claim 3, wherein said central line is an axis of symmetry of said blank and extends through apexes of said V-shaped indentations.

18. The blank according to claim 3, wherein said blank extends continuously and seamlessly from said upper portion to said lower portions via said intermediate portion.

19. The diaper according to claim 1, wherein said first and second positions are spaced from each other in a longitudinal direction of said diaper by a portion of said absorbent.

20. The diaper according to claim 1, wherein said diaper has a crotch region which is located between said first and second positions and which is free of bonding lines.

* * * * *